United States Patent

Reents

[11] Patent Number: 6,073,476
[45] Date of Patent: Jun. 13, 2000

[54] CALIBRATION SAMPLE FOR PARTICLE ANALYZERS AND METHOD FOR MAKING THE SAME

[75] Inventor: William David Reents, Middlesex, N.J.

[73] Assignee: Lucent Technologies Inc., Murray Hill, N.J.

[21] Appl. No.: 09/053,908

[22] Filed: Apr. 2, 1998

[51] Int. Cl.$^7$ .................................................. G01N 17/00
[52] U.S. Cl. .................................................. 73/1.06
[58] Field of Search ................................. 73/1.01, 1.06, 73/28.1, 865.5

[56] References Cited

U.S. PATENT DOCUMENTS

| 5,123,738 | 6/1992 | Yonemura . | |
|---|---|---|---|
| 5,178,836 | 1/1993 | Kitamori et al. | 73/28.01 |
| 5,604,295 | 2/1997 | Robinson | 73/1.06 |
| 5,644,071 | 7/1997 | Wagner | 73/1.06 |
| 5,747,667 | 5/1998 | Sadar | 73/1.02 |
| 5,918,254 | 6/1999 | Bottiger et al. | 73/1.06 |

Primary Examiner—Robert Raevis

[57] ABSTRACT

A calibration sample for a particle analyzer comprises a deposition tube containing a known distribution of submicron size particles. The sample is produced using a microwave discharge in a microwave chamber to generate particles from a feedstock gas at subambient pressure, transporting the particles downstream from the microwave chamber and depositing them on the tube. The downstream tubing can then be removed, stored, transported and used as a calibration sample. In subsequent use, gas flowing through the tube entrains particles from the inner wall, producing a particle-laden gas whose particle size distribution and composition are identical to that produced originally—even after storage for months. The sample, requiring no special equipment, can be used at remote sites to prove-in and calibrate particle analyzers.

10 Claims, 2 Drawing Sheets

CALIBRATION SAMPLE FOR PARTICLE ANALYZERS AND METHOD FOR MAKING THE SAME

FIELD OF THE INVENTION

This invention relates to particle analysis and, in particular, to a portable, stable particle sample for permitting calibration of particle analyzers.

BACKGROUND OF THE INVENTION

Particle analysis is important in a wide variety of industrial processes including the fabrication of high performance semiconductor and optoelectronic devices. As feature sizes on semiconductor devices shrink, the size of particles that causes defects also decreases. On today's advanced devices, particles as small as 0.1 micrometers can cause yield reducing defects. Such particles can come from several sources including delaminating films, broken wafers, atmospheric dust, and the vacuum processes used for the deposition and etching of thin films, especially plasma processes. Analysis of the chemical composition of the particles is an important step in finding the root cause of particle contamination.

There now exist highly accurate techniques for detecting and analyzing sub-micron particles. Such techniques are described in U.S. Pat. No. 5,382,794 issued to S. W. Downey et al. on Jan. 17, 1995 and U.S. Pat. No. 5,631,462 issued to the present inventor W. D. Reents, Jr. on May 20, 1997, both of which are incorporated herein by reference. In essence, the particles are entrained within a gas stream, fragmented and ionized by a laser beam ("laser ablation"), and the chemical nature and concentration of the species within the particle is determined by mass spectrometry. This approach permits real time measurement of particles as small as 1 nm in diameter.

One difficulty impeding wider use of systems for detecting and analyzing such small particles is the need for calibrating them in situ. The equipment is delicate and must be calibrated on the site of use. Typically calibration is accomplished through the use of particle generating systems for producing particles of known size distribution. Such generating systems, however, are expensive specialty devices which are not easily transported. They typically must be disassembled for transportation and reassembled on site, a process which takes several hours at each stage. Alternatively pre-formed particle aggregates can be used in calibration, but specialized equipment is required for de-agglomeration, and the useable sizes are typically in excess of 20 nm. Accordingly there is a need for an improved calibration sample for particle analyzers.

SUMMARY OF THE INVENTION

In accordance with the invention, a calibration sample for a particle analyzer comprises a deposition tube containing a known distribution of submicron size particles. The sample is produced using a microwave discharge in a microwave chamber to generate particles from a feedstock gas at subambient pressure, transporting the particles downstream from the microwave chamber and depositing them on the tube. The downstream tubing can then be removed, stored, transported and used as a calibration sample. In subsequent use, gas flowing through the tube entrains particles from the inner wall, producing a particle-laden gas whose particle size distribution and composition are identical to that produced originally—even after storage for months. The sample, requiring no special equipment, can be used at remote sites to prove-in and calibrate particle analyzers.

BRIEF DESCRIPTION OF THE DRAWINGS

The advantages, nature and various additional features of the invention will appear more fully upon consideration of the illustrative embodiments now to be described in detail in connection with the accompanying drawings. In the drawings.

It is to be understood that these drawings are for purposes of illustrating the concepts of the invention and are not to scale.

DETAILED DESCRIPTION

Figure 1:
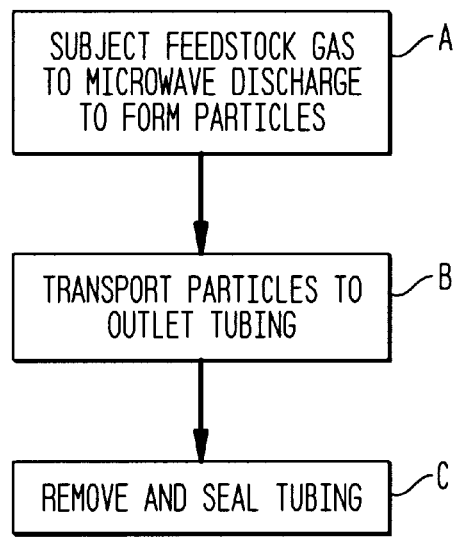
FIG. 1 is a block diagram of a preferred method of making a calibration sample.

Referring to the drawings, FIG. 1 is a flow diagram of a preferred method for making a calibration sample for particle analyzers. As shown in block A of FIG. 1, the first step is to form particles as by subjecting a feedstock gas at subambient pressure to a microwave discharge. The feedstock gases are typically gaseous or volatile organic compounds such as gaseous hydrocarbons, e.g. methane or ethane.

Figure 2:
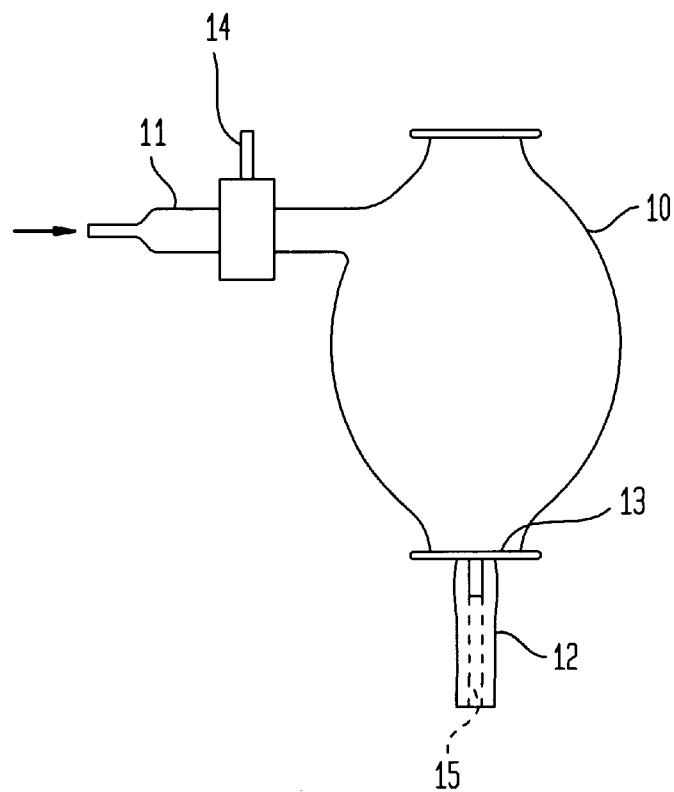
FIG. 2 is a schematic illustration of apparatus useful in practicing the method of FIG. 1.

This step can be better understood by reference to FIG. 2 which illustrates apparatus for practicing the method comprising a diffusion chamber 10 including inlet tubing 11 and the downstream tubing 12 at the outlet 13. The inlet tubing 11, which can be quartz tubing, is surrounded by a microwave cavity 14. In the first step, the diffusion chamber is partially evacuated and feedstock gas passes through tubing 11 within microwave cavity 14 to be subjected to microwave discharge. This generates small particles which enter the chamber 10. Other suitable methods of forming particles are subjecting gas to rf plasma and thermal degradation of organometallics.

The next step, shown in block B, is to transport the particles downstream from chamber 10 into the outlet tubing 12 where they will deposit on the interior walls 15. This transportation is effected by gas flow.

The third step (block C) is to remove the outlet tubing 12 with particles deposited on the interior walls 15. This tubing can be sealed, stored and transported to remote sites for use as a source of particles for calibration.

A particle analyzer is calibrated using the outlet tubing source by connecting the tubing to the analyzer input, passing gas through the tubing to entrain particles from the inner wall 15 of the tubing, and using the analyzer to measure the size distribution and/or composition of the entrained particles. The analyzer is then calibrated to ensure that the measured distribution and/or composition is the same as that measured when the source was originally produced.

The invention can now be better understood by reference to the following specific example.

EXAMPLE

Particles are generated from a methane feedstock gas at pressures in the range 0.01–500 torr (1 torr is typical) in the apparatus shown in FIG. 1. A gas flow rate of 5–25 sccm is used but higher or lower flow rates produce acceptable results. Chamber 10 is constructed of fused quartz to minimize volatilization and to tolerate the high temperatures to which it will be exposed during processing. The microwave cavity 14 surrounds a 5 cm OD quartz inlet tube 11. The cavity is connected to a microwave power supply capable of 100 to 400 W output. In this instance, a 2.45 GHz quarter-wave Evenson cavity is powered by a 200 W Microtron magnetron generator.

The particles are produced in the microwave cavity with a fraction of them being transported downstream and deposited on the inside of tubing 12. A fraction of the particles pass through the tubing 12 and can be analyzed to determine particle size and composition for later use.

The downstream tubing 12 used in this example was ¼" OD polyethylene or stainless steel. The stainless steel tubing produced lower pressure for the reaction.

It was noted that with a flowing gas stream but prior to starting the microwave discharge, particles were not detectable. After particle generation, if the microwave plasma is turned off, particles continue to be present due to shedding from the walls. The size and composition of the shed particles are indistinguishable from the particles detectable during active generation.

For use as a portable calibration sample, the output tubing 12 is preferably stainless steel and has a length in excess of about 6 inches. Lengths of 1–2 feet are typical. The tubing can be sealed for storage and transport using swage-lock fittings.

Figure 3:
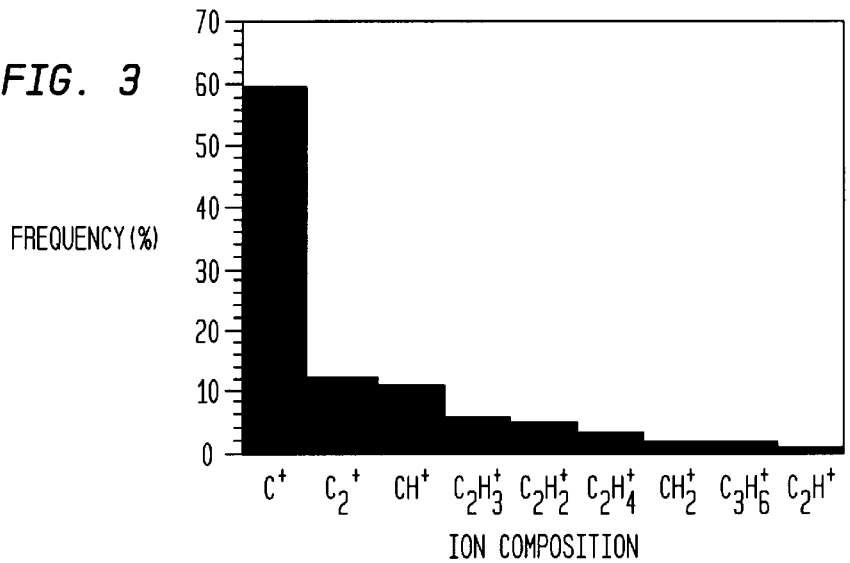
FIG. 3 is a bar graph illustration showing the compositional distribution of ions detected in a typical sample.

FIG. 3 is a bargraph illustration showing the compositional distribution of ions detected from 400 particle generated in a methane plasma. It shows how often each ionic species occurred. More than 60% of the particles have spectra composed of pure carbon.

Figure 4A:
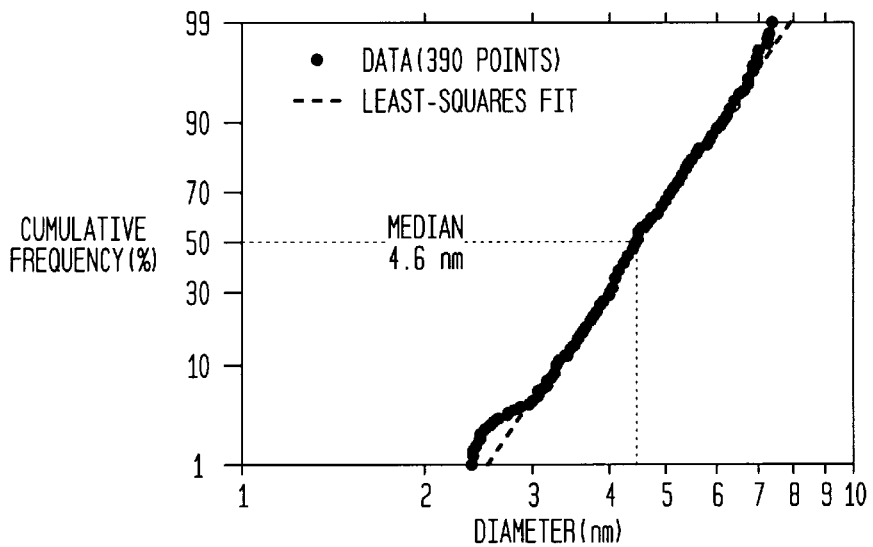
FIGS. 4(a) and 4(b) are graphical illustrations showing, respectively, the cumulative distribution of particle sizes and the probability distribution of particle sizes for a typical sample.
Figure 4B:
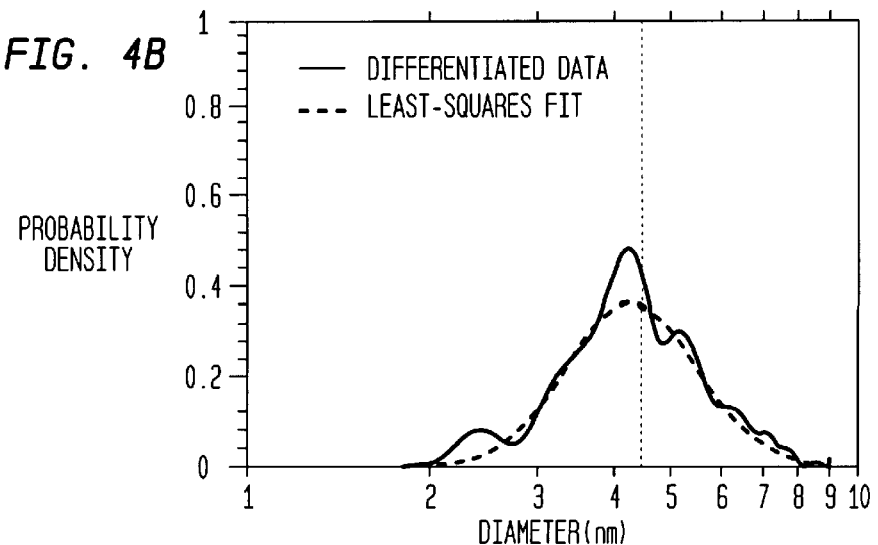

FIGS. 4a and 4b are graphical illustrations of particles prepared as described above, showing, respectively, the cumulative distribution of particles diameters and the probability density distribution for particle sizes. The dashed line in FIG. 4(a) represents the best least-squares fit of a log-normal distribution to the experimental points. The particles have a median size of about 4.7 nm and are predominately distributed in the range 1–10 nm. The dashed line in FIG. 4(b) represents the best fitting lognormal distribution.

It is to be understood that the above-described embodiments are illustrative of only a few of the many possible specific embodiments which can represent applications of the principles of the invention. Numerous and varied other methods and arrangements can be made by those skilled in the art without departing from the spirit and scope of the invention.

What is claimed is:

1. A method for making a calibration sample for a particle analyzer comprising the steps of:
    forming particles by subjecting a feedstock gas to a microwave discharge;
    transporting said particles to a hollow body having an inner wall; and sealing the hollow body.

2. The method of claim 1 wherein said forming step comprises subjecting a gas comprising an organic gas to said microwave discharge.

3. The method of claim 1 wherein said forming step comprises subjecting a gas comprising a gaseous hydrocarbon to said microwave discharge.

4. The method of claim 1 wherein said forming step comprises subjecting a gas comprising methane gas to said microwave discharge.

5. The method of claim 1 wherein said forming step comprises forming particles comprised predominately of submicron diameter particles.

6. A transportable and storage calibration sample for particle analyzers comprising:
    a sealed hollow body having an interior wall;
    adhered to said interior wall of said hollow body a sample of particles, said particles loosely adhered to said wall whereby after opening said sealed body, passage of gas through said body entrains a sample of particles of known size distribution from said wall.

7. The sample of claim 6 wherein said passage of gas entrains a sample of particles having a size distribution predominately in the submicron range.

8. The sample of claim 6 wherein said passage of gas entrains a sample of particles having a size distribution predominately in the range of 0 to 10 nanometers.

9. The sample of claim 6 wherein said passage of gas entrains a sample of particles composed predominately of carbon species.

10. A method for calibrating a particle analyzer comprising the steps of:
    providing a calibration sample in accordance with claim 6, said sample comprised of particles having a measured size distribution
    connecting said sample to the input of said particle analyzer; passing gas through said sample to said particle analyzer, said gas entraining particles from said sample;
    measuring the distribution of particles in said gas by said analyzer; and
    calibrating said analyzer so that the distribution measured by said analyzer corresponds to the known size distribution of said sample.

* * * * *